US 6,621,566 B1

(12) United States Patent
Aldrich et al.

(10) Patent No.: US 6,621,566 B1
(45) Date of Patent: Sep. 16, 2003

(54) OPTICAL INSPECTION SYSTEM HAVING INTEGRATED COMPONENT LEARNING

(75) Inventors: Eric Aldrich, Walnut Creek, CA (US); Richard Pye, Burlington, MA (US); Lyle Sherwood, Pepperell, MA (US); Douglas W. Raymond, Orinda, CA (US); John Burnett, Vacaville, CA (US)

(73) Assignee: Teradyne, Inc., Boston, MA (US)

( * ) Notice: Subject to any disclaimer, the term of this patent is extended or adjusted under 35 U.S.C. 154(b) by 353 days.

(21) Appl. No.: 09/677,290

(22) Filed: Oct. 2, 2000

(51) Int. Cl.[7] ............................................... G01N 21/88
(52) U.S. Cl. ............................... 356/237.1; 356/237.4; 356/237.5; 382/145
(58) Field of Search .......................... 382/147, 141–150; 356/394, 237.1, 237.2–237.5; 348/87

(56) References Cited

U.S. PATENT DOCUMENTS

| 4,908,871 A | * | 3/1990 | Hara et al. ................... 382/147 |
| 5,204,912 A | * | 4/1993 | Schimanski ................. 382/147 |
| 5,555,325 A | * | 9/1996 | Burger ........................ 382/309 |
| 5,564,183 A |   | 10/1996 | Satou et al. |

FOREIGN PATENT DOCUMENTS

| EP | 0 612 203 A1 | 8/1994 |
| EP | 0 685 732 A1 | 12/1995 |
| EP | 0 706 027 A1 | 4/1996 |
| WO | WO 91/13535 | 9/1991 |

* cited by examiner

Primary Examiner—Richard A. Rosenberger
Assistant Examiner—Vincent P. Barth
(74) Attorney, Agent, or Firm—Daly, Crowley & Mofford, LLP (57) ABSTRACT

An automated optical inspection (AOI) system includes component learning integrated with the inspection of a circuit board. The AOI system includes a component learning area that can be viewed by an imaging system used to inspect the circuit board in an inspection area. The component learning area can correspond to a region proximate the inspection area. The automated optical inspection system receives board inspection and component learn requests and determines opportune times to learn new component characteristics during the board inspection process so as to minimize the impact of the learning process on the overall inspection efficiency.

20 Claims, 8 Drawing Sheets

OPTICAL INSPECTION SYSTEM HAVING INTEGRATED COMPONENT LEARNING

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates generally to inspecting objects, and more particularly, to automated optical inspection systems.

BACKGROUND OF THE INVENTION

Automated optical inspection (AOI) systems are used to inspect objects, such as printed circuit boards (PCBs), for a variety of defects. The system can inspect a PCB for proper component presence and orientation, proper solder joint formation, and solder bridges. In one optical inspection application, a system can inspect the toe fillet solder joints of a quad flat pack (QFP) integrated circuit. Such a package has four edges with leads protruding from each edge. Each lead is connected to a pad on the PCB by a solder joint. An incorrectly formed solder fillet will have an appearance that can be detected using well-known image processing algorithms.

Such an AOI system includes a camera head that shuttles back and forth relative to the PCB. The camera head includes an illumination system and one or more cameras. The illumination system may be provided, for example, as one or more light emitting diodes (LEDs), which provide lighting for the purpose of highlighting certain surfaces on the PCB and darkening other surfaces on the PCB to allow the cameras to capture images that are amenable to image processing analysis. Typically, the lights are turned off and on only when the camera head is directly over a region or zone of interest on the PCB. Thus, the illumination system operates as a strobe light. With this strobe light approach, it is not necessary for the camera head to stop in order to acquire an image.

Typically, the board to be inspected is divided into stripes. Each stripe corresponds to a shuttle path along which the camera head travels. Each stripe is divided into fields of view (FOVs). As the camera head shuttles across various portions of the board, the illumination system strobes the lights in accordance with predetermined lighting modes to produce a flow of images from the cameras in the camera head. The images are transferred to memory via framegrabbers for analysis. Exemplary conventional automated optical inspection systems are disclosed in U.S. Pat. Nos. 5,260,779 and 5,260,779, both of which are incorporated herein by reference.

In addition to inspecting a fully assembled circuit board, an optical inspection system can inspect a board at various stages in the assembly process. In the automated manufacture of electronic circuit boards, there are several steps, each of which can be followed by an automated inspection step. The assembly line process can vary, but generally includes applying solder paste, populating the board with components, and heating the board to melt the solder.

Initially, an automatic stenciling machine, a discrete applicator, or other machinery well known in the art of electronic circuit board assembly places solder paste on a bare printed circuit board. The resultant board bears numerous dots of solder paste, which can be in the form of rectangular prisms known as "bricks." The solder bricks can be inspected in a conventional manner to verify correct location and volume.

Another automated machine, such as a so-called chip-shooter or a pick and place machine, then places components on the board with the component electrical terminations or leads in contact with the bricks. The populated board can be inspected to verify that all components have been correctly positioned.

The board then passes through a heating system (e.g. a hot oven) to melt the solder bricks and form metallurgical bonds between the electrical terminations of the components and the plated metal pads of the printed circuit board. The assembled board can be inspected to verify that the solder joints are properly formed and that all components are still correctly placed.

One disadvantage associated with conventional optical inspection systems is the time and cost associated with the system learning the characteristics of new circuit board components. Before an optical inspection machine can inspect a particular type of board, the machine needs to learn the characteristics of each component on the board. Typically, the system is programmed in a manner that includes a "learning" step in which the inspection machine views each component and records digitized images of its appearance. These stored images, and/or attributes extracted from them, are used to generate models for the components against which the board components are compared while the machine inspects boards in a production environment.

As known to one of ordinary skill in the art, component learning can be a slow and burdensome process requiring fixturing (the fabrication of test fixtures), significant manual labor, and considerable time spent on the inspection machine itself. In addition, the inspection system is typically removed from the production inspection process to learn a new component. Thus, the whole assembly line must be stopped while the inspection system learns one or more new components thereby decreasing the overall production assembly efficiency.

It would, therefore, be desirable to provide an optical inspection system that reduces the time and cost associated with the inspection system learning the characteristics of new circuit board components. It would also be desirable to provide an inspection system that improves the overall efficiency of the inspection process on a production assembly line.

SUMMARY OF THE INVENTION

The present invention provides an automated optical inspection system that learns the characteristics of a new component as part of the overall inspection process. By integrating the component learning process into the inspection process, the overall inspection efficiency is enhanced. Although the invention is primarily shown and described in conjunction with an automated optical inspection system for printed circuit boards, it is understood that the invention is applicable to other inspection applications in which the characteristics of new components and objects need to be acquired from time to time.

In one aspect of the invention, an automated optical inspection (AOI) system for inspecting circuit boards includes a component learning area in which the characteristics of one or more components can be learned. In one embodiment, the component learning area is adjacent an inspection area in which the circuit boards are inspected. The component learning area can be imaged by one or more cameras used to provide images of the circuit board. The system integrates image acquisition of the circuit board with image acquisition of the new components so as to minimize the impact of the component learning process on the overall inspection process.

In an exemplary embodiment, the component learning area corresponds to a region that can be imaged by the camera(s) used to image the circuit board but is not used by the system for the inspection of boards. While the component learning area can be imaged by the camera(s), the camera support structure can prevent a board from reaching the component learning area. More particularly, the circuit board enters and exits the inspection area though passages defined by the system support structure, which can include pillars used to support the camera head assembly. The component learning area can be adjacent the inspection area and "behind" the pillars, which is not accessible to the board.

In a further aspect of the invention, an automated optical inspection system receives requests for inspection of boards and learning of new components. The system determines opportune times for learning the new components during the board inspection process. Opportune times includes times during which boards are being loaded and unloaded, times at which camera path for inspecting the boards is proximate the component learning area, and times at which there are no board inspection requests. Opportunistic learning of new components minimizes, or eliminates, the impact of component learning on the overall board inspection process efficiency.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
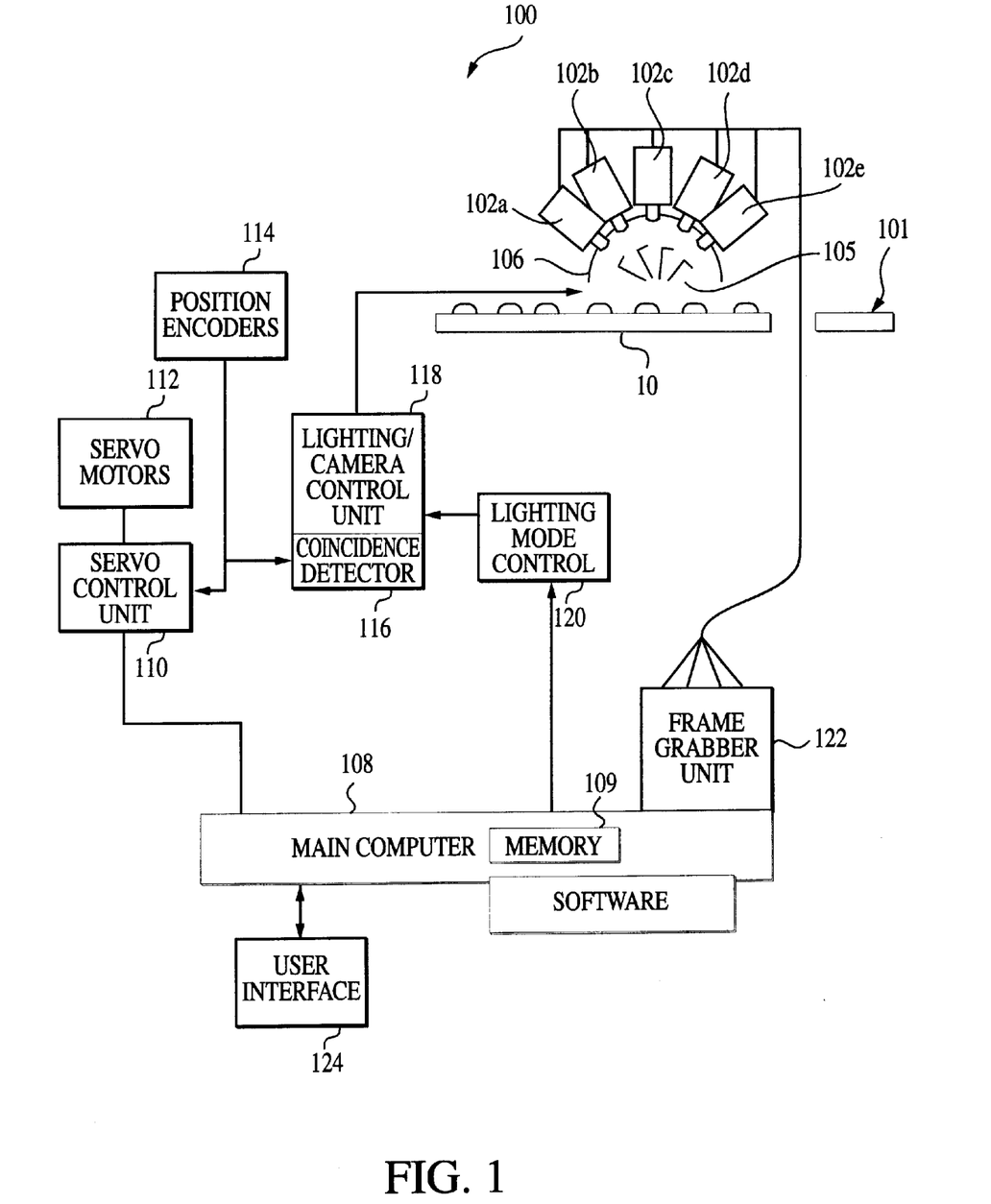
FIG. 1 is a schematic depiction of an exemplary automated optical inspection (AOI) system having a component learning feature in accordance with the present invention.

FIG. 1 shows an exemplary embodiment of an automated optical inspection (AOI) system 100 having component learning integrated with the inspection process in accordance with the present invention., In general, the system 100 includes a component learning area 101 for learning the characteristics of new components during the inspection of an object, such as a printed circuit board 10. This arrangement significantly improves the overall assembly process efficiency in comparison with conventional inspection systems.

The optical inspection system 100 can include one or more cameras 102 for providing images of the printed circuit board 10 to be analyzed with well-known inspection algorithms. In one embodiment, the system 100 includes a plurality of cameras 102a–102e for providing images of the printed circuit board 10 and components in the component learning area 101. The cameras 102a–102e move along a predetermined path, e.g., so-called stripes, to image desired portions of the board. An illumination system 105, disposed about a dome-shaped assembly 106 illuminates the PCB 10 in a desired manner. The camera/dome assembly moves so as to image an inspection area in which the circuit board 10 is disposed as well as components in the component learning area 101.

In one particular embodiment, the illumination system 105 comprises a plurality of light emitting diodes (LEDs) arranged in a matrix disposed on the dome-shaped assembly 106. In an exemplary embodiment, five cameras 102a–e are used. Four of the cameras 102a, 102b, 102d and 102e are disposed at an angle, e.g. thirty degrees with respect to a normal to a surface circuit board 10, and the fifth camera 102c is located directly over (vertical) the circuit board 10. The cameras 102a–102e can be secured to the dome assembly 106, which is moved across stripes of the board.

While an exemplary embodiment of the invention moves the cameras 102a–102e and lighting system 105 with respect to the circuit board and/or the components to be learned, one of ordinary skill in the art will readily appreciate that the board and/or component position can be manipulated in relation to the cameras without departing from the invention. It should also be appreciated that although five cameras are here shown, fewer or more than five cameras can be used.

Figure 1A:
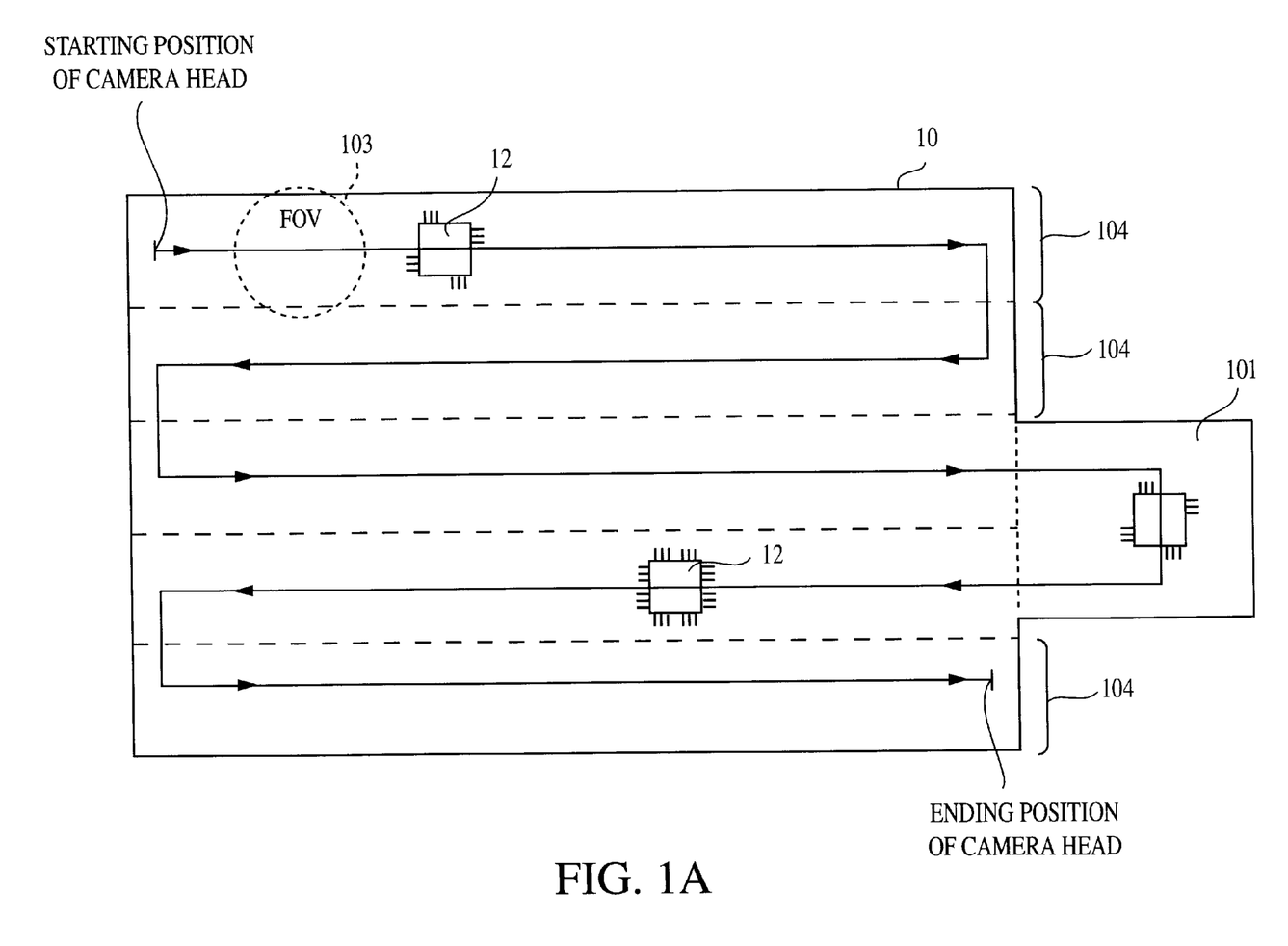
FIG. 1A is a schematic depiction of the AOI system of FIG. 1 showing a circuit board inspection integrated with component learning in accordance with the present invention.

Referring briefly to FIG. 1A, the system 100 divides the PCB 10 into so-called stripes 104, which are subdivided into fields of view (FOVs) 103 that are analyzed to identify manufacturing defects associated with a PCB populated with circuit components 12, such as non-conforming solder joints. The cameras move along the stripes to acquire the desired image data. At any given time, each camera will have a predetermined FOV 103 corresponding to the position of the camera with respect to the PCB or a new component. Fields of view (FOVs) within the stripes are imaged by one or more of the cameras 102. Partitioning a circuit board into stripes and FOVs is well known to one of ordinary skill in the art. In accordance with the present invention and as described more fully below, the path followed by the camera head can include entry into the component learning area 101 as part of the board inspection process. Since the inspection stations can be a bottleneck in a production environment, integrating component learning with board inspection to decrease the overall board inspection time, as compared with known optical inspection systems, is a significant feature of the automated inspection system of the present invention.

Referring again to FIG. 1, based upon the inspection program, the main computer 108 provides commands to a servo control unit 110, which controls the servo motor 112, to effect positioning of the dome 106 over each stripe of the circuit board 10 or component learning area 101. In an exemplary embodiment, the dome 106 is moved over the stripe and the LEDs 105 are strobed to illuminate the board/new component for a particular one of the cameras 102a–102e. The actual position of the dome assembly 106 is determined by a position encoder 114. In one embodiment, the encoder 114 includes a pick-off type system having a linear encoder that generates digital quadrature signals providing a resolution of about five millionths of a meter. The digital servo control unit 110 receives the digital encoder signals and provides the necessary motor drive signal corrections to properly position the dome assembly 106 across a stripe. Such positioning and tracking of the dome assembly 106 is well known to one of ordinary skill in the art.

A coincidence detector 116 receives dome position information from the position encoders 114. The coincidence detector 116 compares the encoder dome position information to a position provided by the computer 108 and stored in the event memory at which one or more of the cameras 102a–102e are to be fired. When the coincidence detector 116 detects a match, a lighting/camera control unit 118 is notified and fires one or more of the cameras 102a–102e and activates selected LEDs in accordance with predetermined lighting mode information contained in the lighting mode control unit 120.

The system 100 further includes a frame grabber unit 122 that receives image data from each of the cameras 102a–102e and stores the data in a memory 109. In general, this arrangement allows the main computer or processor 108 to analyze the image data in the memory 109 for proper assembly, component identity and position, and solder joint quality as part of the board inspection and to learn characteristics for new components.

While the invention is shown as having a main computer, it will be readily apparent to one of ordinary skill in the art, that the system can include further processors, such as a component learning processor for determining opportune times to perform component learning as described below. It is understood that the functionality of the AOI system can be implemented in a variety of architectures.

A user interface 124, such as a graphical user interface (GUI), coupled to and cooperative with the main computer 108 allows a user to implement a desired production scheme and also allows the user to manually run selected inspection programs for a circuit board that requires additional attention. The user interface 124 can also allow the operator to control the component learning process as described below.

Figure 2:
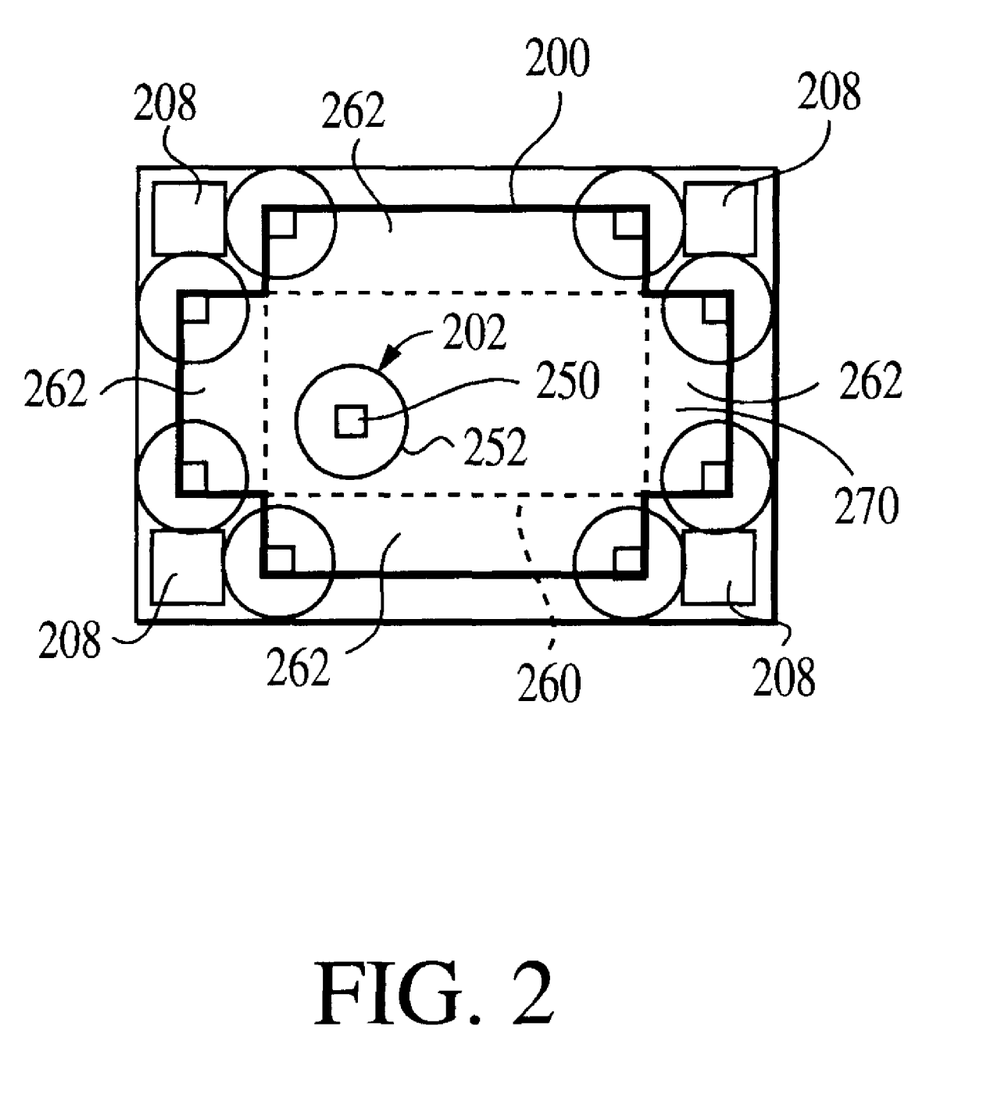
FIG. 2 is a schematic depiction of a component learning area in accordance with the present invention for the AOI system of FIG. 1.
Figure 2A:
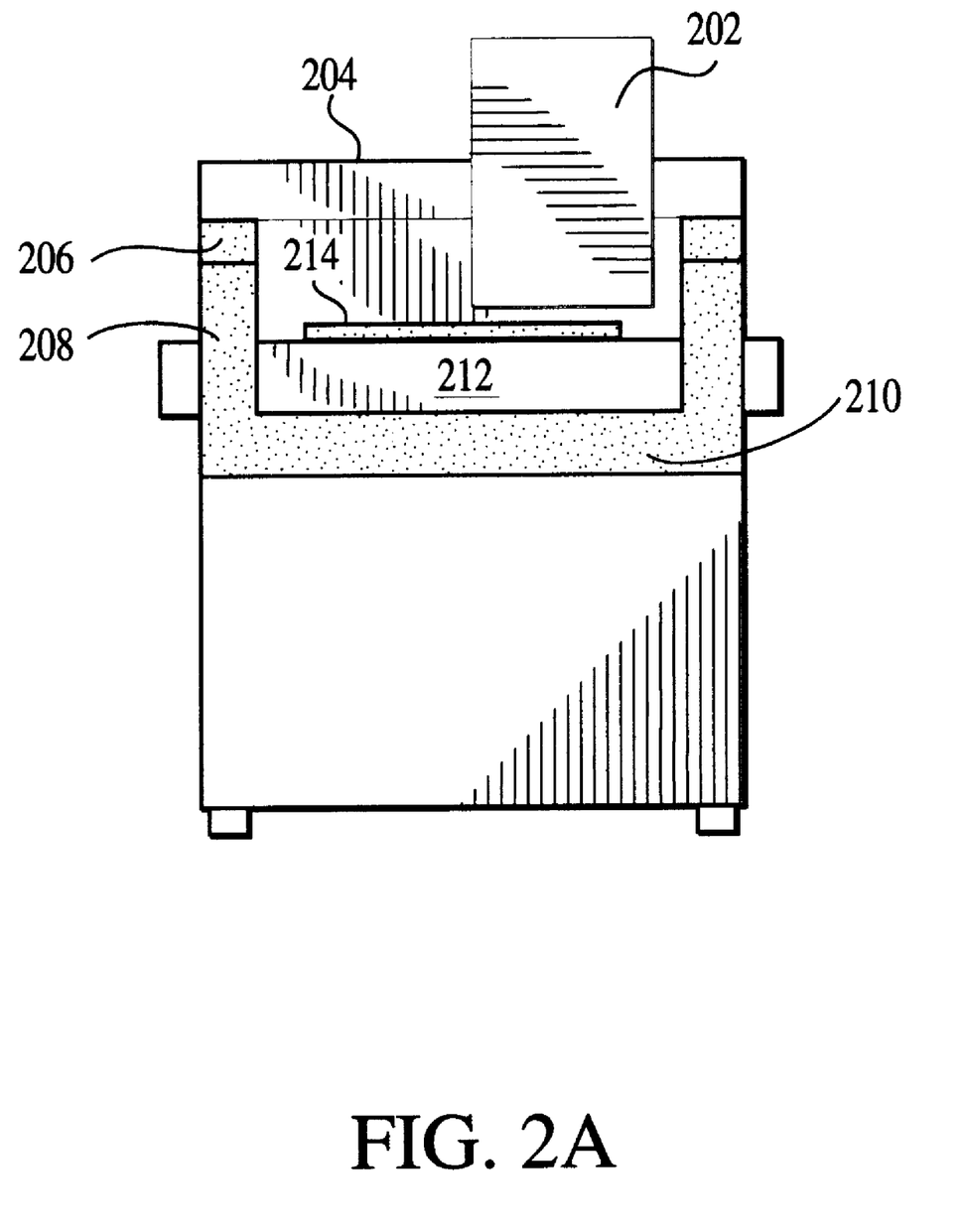
FIG. 2A is a schematic depiction of a front view of the AOI system of FIG. 2.
Figure 2B:
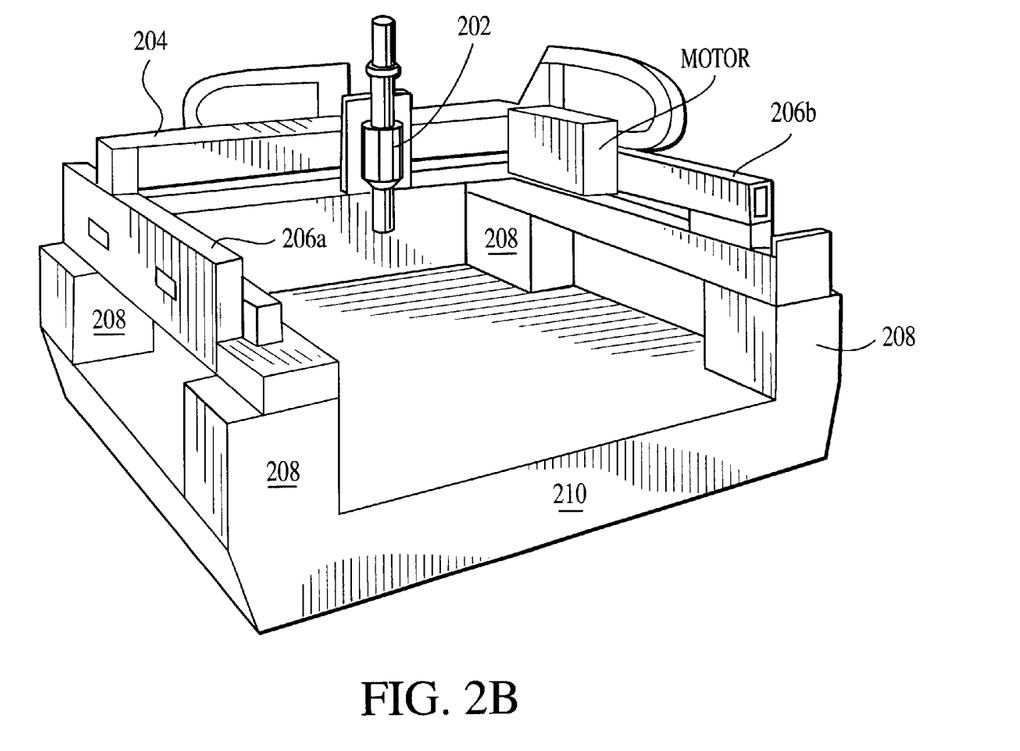
FIG. 2B is a perspective view of an exemplary camera assembly support structure for the AOI system of FIG. 1.

As shown in FIGS. 2–2B, the outermost boundary 200 of where a camera head assembly 202 can travel is limited by the structure that supports the camera and camera head assembly. In one embodiment, the camera head is mounted on a gantry cross beam 204 supported by main rails 206a,b. The main rails 206 are supported by pillars 208 that can be located at corners of a base assembly 210. A series of motors, such as those shown and described in conjunction with FIG. 1, move the gantry beam 204 in a first direction along the main rails 206 and move the camera head 202 in a second direction along gantry beam 204. A conveyor assembly 212 can facilitate the loading and unloading of a circuit board 214 to be inspected.

A camera head having a square field of view (FOV) 250 is surrounded by a dome 252 supporting a lighting system for illuminating the board under inspection in a desired lighting mode. The camera head 202 motion is primarily limited by the location of the pillars 208 and also the base 210 and rails 206. That is, the dome assembly 252 should not collide with the pillars 208 at the corners of the base assembly 210. Since the pillars 208 should be avoided, the range of motion of the camera head 202, i.e., the boundary 200, defines a cross shape having an inner rectangle 260 and a series of areas 262 that can be imaged by the camera. These areas 262 are not used for inspecting a circuit board since the board dimensions must allow the board to enter the inspection area without hitting the pillars. Thus, the system inspection area corresponds to the rectangle 260.

In an exemplary embodiment, a component learning area 270 corresponds to one of the areas 262 outside the rectangle and inside the cross that can be imaged by the camera. The component learning area 270 can be any of the surplus areas 262 provided that the loading and unloading of circuit boards into the inspection area is not impeded. It is understood that the system can include a plurality of component learning areas.

In an alternative embodiment, the main rails are supported on flanges rising out of the base in stead of pillars. This arrangement can include a "parking strip" in a surplus area into which the camera can be moved so that it is not falsely detected as a circuit board in the conveyor mechanism.

It is understood that the automation of the learning process can vary from fully automated to fully manual with many semi-automated variations. In general, new components are placed within the component learning area and imaged to acquire characteristic data for the new components. This data is used to generate a model against which board components are compared. Once the component is learned, a board having the learned component can be inspected by the system. A fully automated learning process can include programming and loading the inspection system and conveyors with a series of boards to be inspected and a series of components to be learned. In addition, the system can optimize the overall inspection and learning process, as described below.

Figure 3:
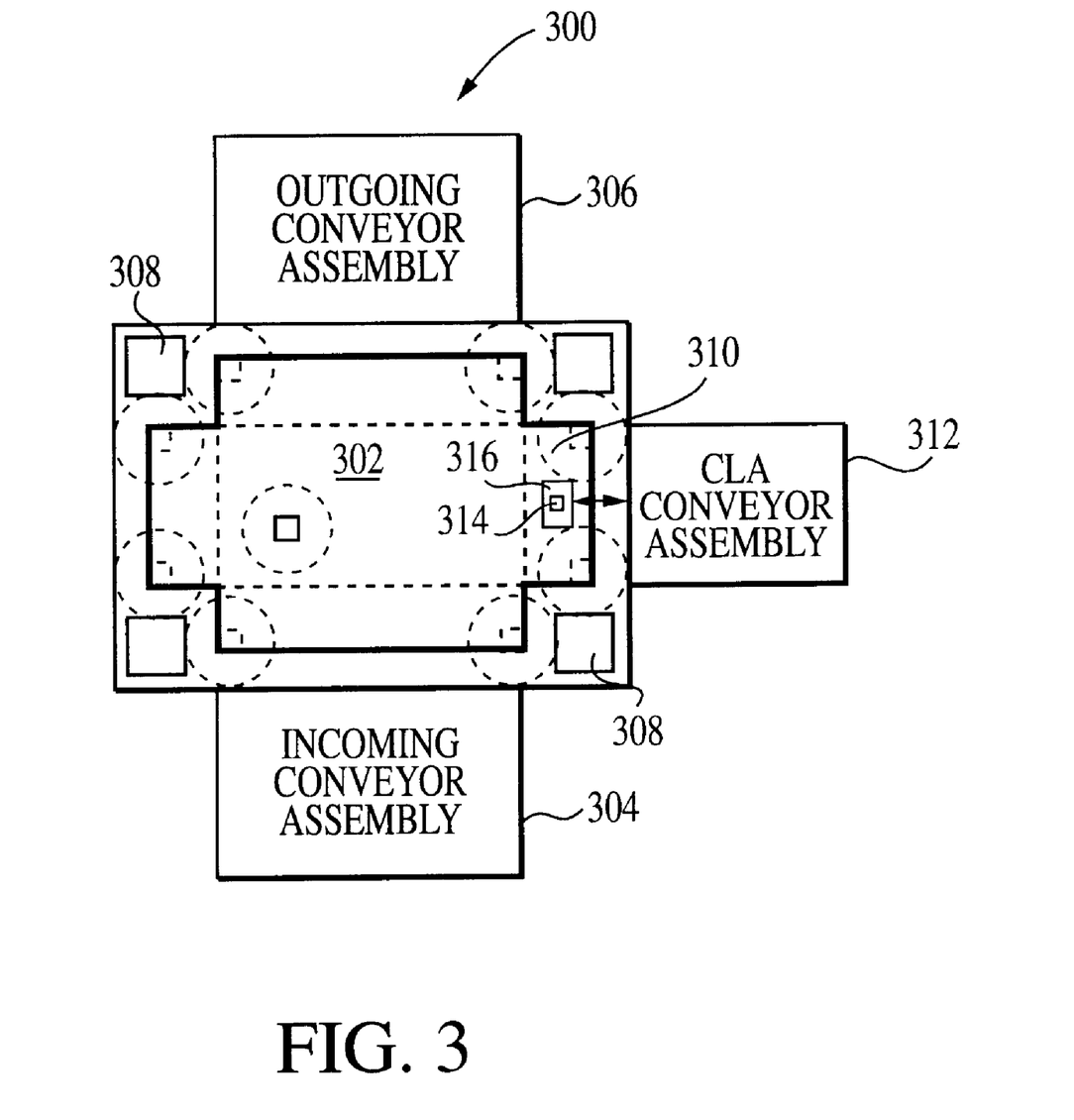
FIG. 3 is a schematic depiction of an AOI system having automated component learning in accordance with the present invention.

FIG. 3 shows an automated optical inspection system 300 having an automated component learning capability in accordance with the present invention. Circuit boards are loaded and unloaded into an inspection area 302 via respective conventional incoming and outgoing conveyor assemblies 304,306. The pillars 308 at the corners of the support structure determine the lateral dimensions of the inspection area 302 and a component learning area 310, as described above.

The system 300 includes a component learning area (CLA) conveyor assembly 312 for loading and unloading components 314 into the component learning area 310. The component 314 can be placed on a platform 316 to facilitate imaging of the component. In one embodiment, an operator positions one or more components to be learned by the system on the platform. The CLA conveyor 312 under the control of the main computer 108 (FIG. 1), moves the platform 316 into the learning area 310 for image acquisition. Once the desired images of the new component are acquired, the CLA conveyor 312 removes the platform from the learning area. The operator can then place further components on the platform for learning by the system.

In an alternative embodiment (not shown), an operator manually loads and unloads components into the learning area. In this arrangement, the system can stop the servos that move the camera head during manual loading of the platform. A system of interlocks can prevent the camera head servos from moving while the operator's hand is in the machine. In another embodiment, an opening for the platform is sized to allow the loaded platform into the learning area while preventing an operator from placing a hand through the opening. This arrangement may obviate the need to stop the camera head. During manual operation, the operator cooperates with a system interface, such as graphical user interface (GUI), to ensure proper and timely component loading and unloading.

The platform used to support the components to be learned can be provided in a variety of structures in accordance with the needs of a particular component or characteristic acquisition. One type of platform includes a relatively simple blank platform on which a component can be placed by hand. A guide can be provided to help establish a position and orientation for the component. Double-sided tack tape can be used to hold the component more firmly. The platform can also include a stage for accepting small coupons, each which can carry one of more components to be learned. The coupon can include a small printed circuit board with plated pads similar to those on which the component to be learned will be mounted during inspection. Solder paste can be stenciled onto the pads in order to give the closest possible impression of the picture to be acquired during inspection. In addition to components, the platform can also include other objects, such as a white balance target, and/or a 3D alignment target, to facilitate the learning process.

It is understood that one or more components can be placed in the component learning area at any one time for image acquisition by the camera. It is further understood that more than one type of component can be placed within the component learning area and "learned." In addition, the system can include a plurality of component learning areas located in regions that are accessible to the camera(s) while not interfering with the loading and unloading of boards to be inspected.

In a further embodiment, once a component image is learned, the system stores and transmits the component characteristics to other networked inspection systems. In this way, only one inspection system in the production environment needs to spend time learning a new component. In one embodiment, the characteristics of new components are stored in a library file on the network. Each of the inspection systems can examine the new component library file in the event that a board to be inspected contains a component for which the system does not have the characteristic data. In one embodiment, one system operated by a senior technician, for example, handles the bulk of the component learning. The learned component data can then be accessed by the other systems.

The parameters associated with learning a component can vary depending upon the requirements of a particular application. Exemplary component parameters include the part shape, part description, part geometry, pad geometry, orientation marks, feature descriptions, known part numbers associated with the new shape, and initial orientation. As will be readily apparent to one of ordinary skill in the art, certain parameters can be provided by an operator and certain other parameters can be learned. For example, the operator can provide a name and package type for the new component to which the acquired parameters will be associated. In addition, certain parameters, such as parameters having a range of values, can be modified by an operator after the learning process. Further, an operator can define one or more regions of interest for the component.

In one embodiment, an operator places a component to be learned in the component learning area and inputs a name and package type for the component into the system via a user interface. The package type can indicate, for example, the number and location of component leads. The operator can then associate various characteristics to the model, such as body type, orientation marks, lead groups, and pads. Tolerance ranges for the various component characteristics can be adjusted by the operator.

The system then learns the component as images of the component are acquired. More particularly, the system can identify, count, and locate the component leads to estimate the lead pitch for generating an initial package object or model. The system can request the operator to confirm the characteristics of the generated model to complete the learning of the component.

Figure 4:
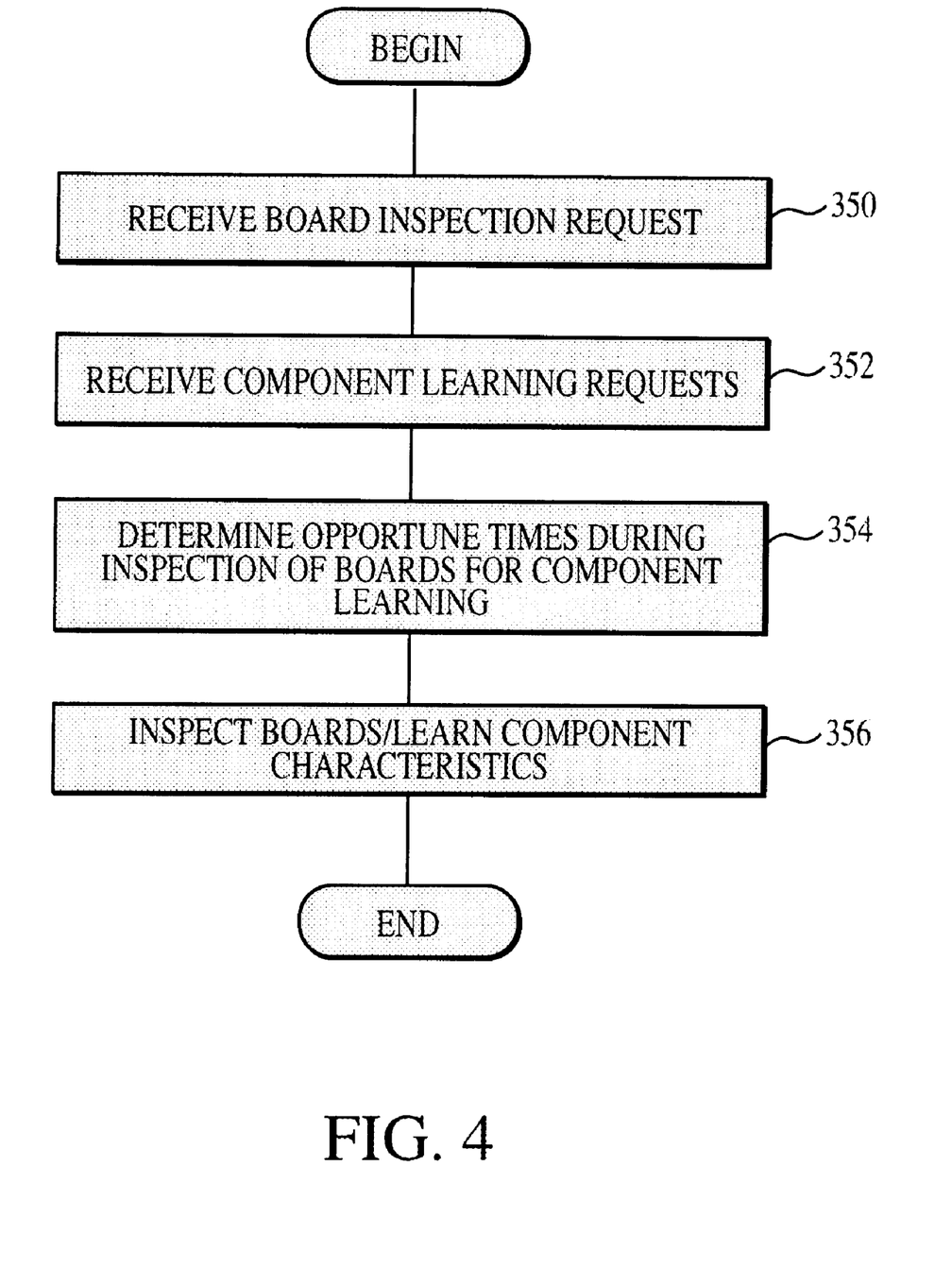
FIG. 4 is an exemplary flow diagram showing component learning integrated into the inspection process in accordance with the present invention.

FIG. 4 shows an exemplary sequence of steps for integrating component learning with board inspection in accordance with the present invention. In step 350, the processor receives board inspection requests from an operator for example. The request can optionally include information as to the type and number of boards to be inspected by the machine. In step 352, the system receives requests for learning of new components. In one embodiment, the component learning requests are generated by the system based upon the components on the boards in the board inspection request.

In step 354, the system determines opportune times for learning new components during the board inspection process to minimize the impact on the board inspection process. In general, the term "opportune time" refers to a time in which (1) the operator has named the type of component currently sitting on the component learning platform and provided parameters necessary to the learning process; (2) the operator has commanded the machine to learn the component (s); and (3) the machine is in a condition where it can take the picture with minimal interference with the timely inspection of a production board. In step 356, the system inspects the requested boards and opportunistically learns the new components in an integrated fashion.

The time at which the camera visits the component learning area can vary in accordance with the operating environment. For example, the camera can image, e.g., learn a new component while the inspection system is idle, e.g., has no incoming boards to be inspected. In another embodiment, the new components are learned during the time in which a board is being fed out of the system and another is being fed in, as described below. In the case where the camera can visit the component learning area while the system waits for a board to enter the inspection area, there may be no impact at all on the time required to inspect the board. In a further embodiment, the camera visits the component learning area while the system is inspecting a board. In this case, the camera can enter the component learning area when the inspection path of the board, e.g., the stripes, takes the camera in proximity to component learning area as shown in FIG. 1A. The overall impact of learning new components while inspecting a board in this way is relatively minor.

Where the camera is multiplexed or interleaved between board inspection and component learning, it is understood that priority, e.g., the amount of time allotted, for component learning can be adjusted based upon a variety of factors including production priority, production quotas, and the number of boards with new components. In general, the time allotted to the learning process while boards are being inspected can be relatively generous or relatively stingy. For example, the learning priority can be set at one extreme (stingy) such that the inspection of boards is never interrupted for learning new components. The learning priority can be incrementally increased to allow component learning within specified limits. The priority adjustment can be set manually by an operator or automatically in software based upon a variety of parameters, such as numerical targets for inspected boards. In the case where an operator manually places new components in the learning area, learning priority can be set to provide an operator a predetermined time to place components in the learning area. In the case where a machine is the slowest in the assembly line, the operator can minimize or eliminate entirely the amount of time for learning new components. In addition, learning can be limited to every Nth board. For a machine that is ahead of schedule, the operator can increase the component learning time in the overall board inspection process.

For example, the system may require about two minutes to learn a certain component. When the production volume is relatively low, the system may be available for relatively long stretches of component learning activity between one production inspection event and the next. When production volume is relatively high, the system can be largely occupied with production activity, and its availability for learning can be limited. Under some circumstances, for example, near the end of an accounting period when a production goal is measured, a manager can choose to devote the system entirely to production inspection.

Alternatively, the system can be programmed to learn a new component every N production boards. The value for N can be adjusted manually by the operator or it can be adjusted by the computer based upon production volume and proximity to the end of the quarter, for example. In the event that new board types are to be inspected, the amount of component learning can increase dramatically. Well before the end of a production period, an operator can assign a relatively high priority to component learning to avoid a production bottleneck at the end of the production period due to unlearned components.

In one embodiment, fuzzy logic is used to provide an automated learning priority decision. For example, fuzzy logic variables can include ProductionVolume (high or low);
LearningAvailability (high, low or zero);
QuarterEnd (close or not close);
A sample set of rules follows:
If ProductionVolume is Low then make LearningAvailability high;
If ProductionVolume is High then make LearningAvailability low;
If QuarterEnd is Close and ProductionVolume is high, then make LearningAvailability zero;

An operator can define "high" and "low" for the fuzzy variables ProductionVolume and LearningAvailability. For example:

ProductionVolume is "high" when over 100 boards per hour;
ProductionVolume is "low" when under 20 board per hour;
QuarterEnd is June 30;
Close is 3 days;

The LearningAvailability variable can then be processed as follows:

If LearningAvailability is high then allow a 2-minute learning period to begin any time when the machine is idle;
If LearningAvailability is low then allow a 2-minute learning period to begin once each hour;
If LearningAvailability is zero then allow no learning periods.

This simple fuzzy logic implementation allows the system to automatically decide when it should make itself available for a learning period and when it should not. The board inspection rate can be taken into account to measure the fuzzy variable ProductionVolume without human intervention. By referring to its internal clock-calendar, the system can determine how far it is from the end of the calendar quarter. When it evaluates the rules and determines that it is on an hourly schedule, the system can schedule the learning appointment in advance, and notify the operator when the results will be available.

In general, the system takes the current learning priority into account and determines opportunistic times for component learning. As described above, opportunistic times include system idle time and times during which the stripe path 104 for the board to be inspected is proximate the component learning area. At such opportunistic times, the camera can enter the component learning area and acquire image data of the new component as shown in FIG. 1A. The number of times the camera deviates from the board stripe path and the duration of the deviation is based upon a variety of factors that can include learning priority, as described above.

Figure 5:
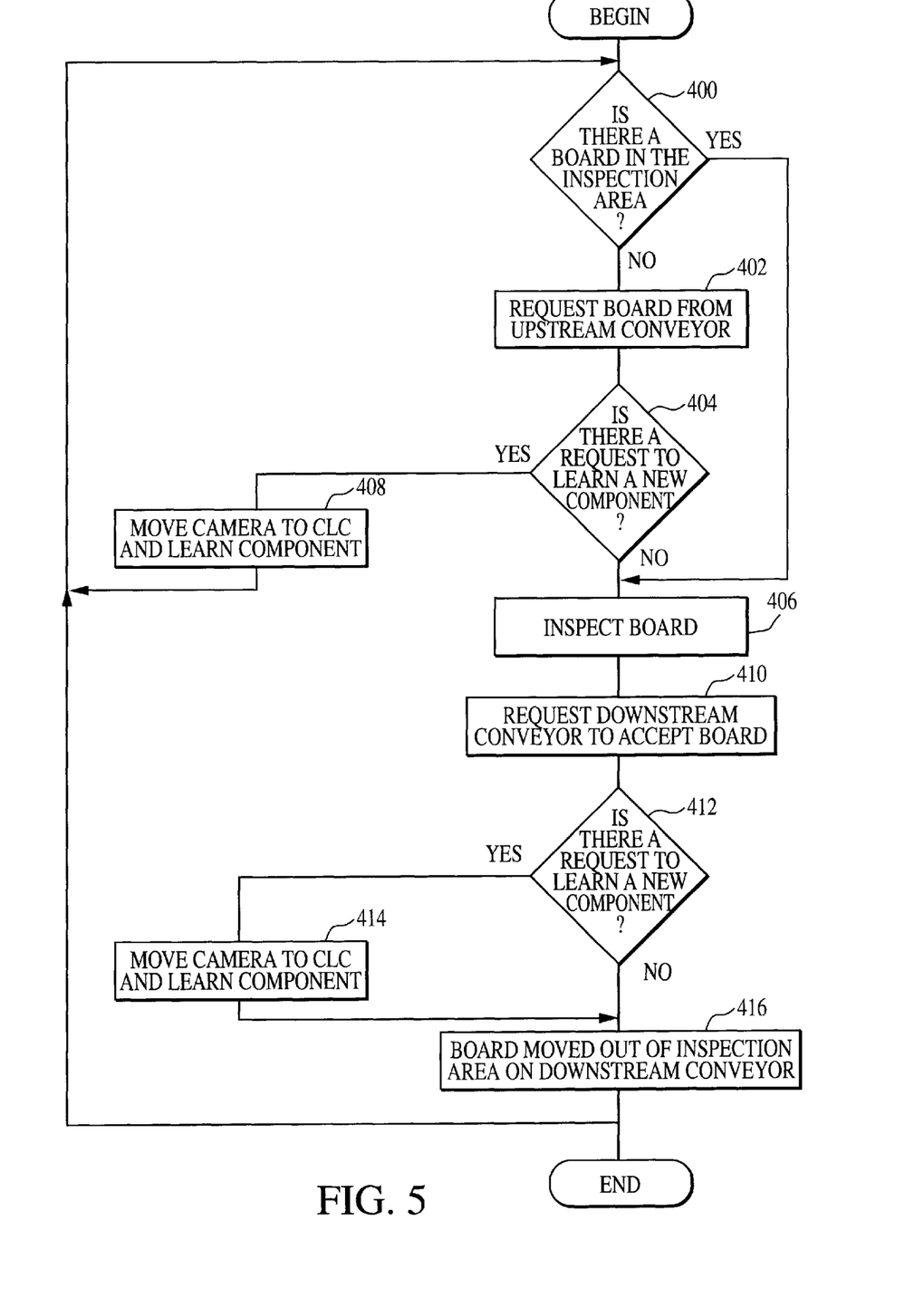
FIG. 5 is an exemplary flow diagram showing component learning during the loading and unloading of boards to be inspected in accordance with the present invention.

FIG. 5, in combination with FIG. 3, show an exemplary sequence of steps for integrating the learning of new components during the loading and unloading of boards to the inspection area in accordance with the present invention. In step 400, it is determined whether there is a board in the inspection area 310. If there is not a board in the inspection area, the processor 108 (FIG. 1) sends a request to the incoming conveyor assembly 304 in step 402. If there is a board in the inspection area, the board is inspected in step 406. After sending the request for an incoming board, the system determines whether there is a request to learn a new component in step 404. If there is such a request, in step 408 the camera moves to the component learning area to acquire characteristic data for the component to be learned.

Once the board is inspected in step 406, the processor sends a request to the outgoing conveyor 306 to accept the inspected board in step 410. In step 412, the system determines whether there are further or incomplete learning requests. In step 414, the camera moves to the component learning area if a learning request is found in step 412. In step 416, the board is moved out of the inspection area via the outgoing conveyor 306.

Where a series of new components are to be learned, an operator can enter the preliminary component data offline and store them in a learn file. The operator can then collect samples of the new parts from stock. In one embodiment, the operator selects a mode of operation for learning and/or inspection. The mode can include multiplexed inspection and learning with the inspection priority set to a desired level as described above.

When the inspection process is initiated, the processor searches for the learn file. the operator is informed of the next component to be learned via a display, for example. At a convenient time, the operator can locate the correct part and provide an indication to the system, e.g., click on a display icon, to activate the learn cycle at the next opportune time, e.g., while waiting for a board to enter the inspection area. When the component is learned, the display can indicate that the machine is ready for the next component(s).

Thus, where one type of board to be inspected has new components that must be learned by the system prior to inspection, other types of boards having known components can be inspection while the system learns the new components. When the components are learned, the boards having these newly learned components can be inspected.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An automated optical inspection system, comprising:
   a base having an inspection area for supporting a circuit board to be inspected and a learning area for supporting a component having characteristics to be learned by the system;
   a camera assembly supporting a camera for imaging the circuit board in the inspection area and the component in the learning area; and
   a processor coupled to the camera assembly for integrating image acquisition of the circuit board and the component.

2. The system according to claim 1, further including an incoming conveyor assembly for loading boards into the inspection area and an outgoing conveyor assembly for unloading boards from the inspection area.

3. The system according to claim 2, further including a learning conveyor assembly for loading and unloading components into the learning area.

4. The system according to claim 3, further including a support structure for supporting the camera assembly, the support structure preventing the boards from entering the learning area.

5. The system according to claim 4, wherein the support structure includes pillars extending from the base that determine a boundary of the inspection area and the learning area.

6. The system according to claim 1, further including at least one additional learning area.

7. The system according to claim 1, further including a support structure supporting the camera assembly having a plurality of pillars extending from the base, wherein a boundary of the inspection area and the learning area corresponds to an outermost path of the camera assembly that avoids the pillars.

8. The system according to claim 7, wherein the learning area is located between first and second ones of the plurality of pillars.

9. The system according to claim 8, wherein the first one of the plurality of pillars is proximate an incoming board conveyor assembly and the second one of the plurality of pillars is proximate an outgoing board conveyor assembly.

10. An automated optical inspection system for inspecting a circuit board having integrated component learning, comprising:
    a camera head assembly including a camera and an illumination system;
    a support structure supporting the camera head assembly, the support structure including a plurality of pillars;
    a base having an inspection area for inspecting circuit boards and a learning area for learning a new component, the plurality of pillars extending from the base, wherein the camera assembly can move to image the circuit board in the inspection area and the component in the learning area;
    a processor for controlling camera image acquisition to integrate board inspection and component learning.

11. The system according to claim 10, wherein first and second ones of the plurality of pillars define an entrance for circuit boards into the inspection area and third and fourth ones of the plurality of pillars define an exit for circuit boards out of the inspection area such that the circuit boards do not enter the learning area.

12. The system according to claim 11, wherein the learning area is disposed between the first and third ones of the plurality of pillars.

13. A method of integrating circuit board inspection with learning new components, comprising:
    placing a circuit board into an inspection area;
    placing a component to be learned by the system into a learning area; and
    multiplexing image acquisition of the circuit board and image acquisition of the component.

14. The method according to claim 13, further including acquiring images of the component at opportune times.

15. The method according to claim 14, wherein the opportune times include times at which there is not a pending request to inspect a circuit board.

16. The method according to claim 14, wherein the opportune times include times during which further circuit boards are being loaded and unloaded from the inspection area.

17. The method according to claim 14, wherein the opportune times include times during inspection of the circuit board at which the camera is proximate the learning area.

18. The method according to claim 14, further including setting a priority for learning components.

19. The method according to claim 18, wherein the setting for learning priority can include a predetermined time range adapted to prevent interruption of inspecting circuit boards.

20. The method according to claim 19, wherein the setting for learning priority can range from no interruption of inspecting circuit boards to allotting a predetermined amount of time for learning the components.

* * * * *